(12) United States Patent
Socci

(10) Patent No.: US 9,399,010 B2
(45) Date of Patent: Jul. 26, 2016

(54) NAIL ENAMEL COMPOSITIONS HAVING DECORATIVE VOIDS

(71) Applicant: Kirker Enterprises, Inc., Paterson, NJ (US)

(72) Inventor: Robert L. Socci, Cedar Grove, NJ (US)

(73) Assignee: Kirker Enterprises, Inc., Paterson, NJ (US)

( * ) Notice: Subject to any disclaimer, the term of this patent is extended or adjusted under 35 U.S.C. 154(b) by 159 days.

(21) Appl. No.: 13/788,235

(22) Filed: Mar. 7, 2013

(65) Prior Publication Data

US 2014/0255325 A1  Sep. 11, 2014

(51) Int. Cl.
*A61K 8/891* (2006.01)
*A61Q 3/02* (2006.01)
*A61K 8/58* (2006.01)

(52) U.S. Cl.
CPC .............. *A61K 8/891* (2013.01); *A61K 8/585* (2013.01); *A61Q 3/02* (2013.01)

(58) Field of Classification Search
None
See application file for complete search history.

(56) References Cited

U.S. PATENT DOCUMENTS

| | | | |
|---|---|---|---|
| RE16,760 E | 10/1927 | Egelhoff | |
| 1,689,892 A | 10/1928 | Boot | |
| 1,732,661 A | 10/1929 | Boot | |
| 2,021,152 A | 11/1935 | Neuhaus | |
| 2,248,254 A | 7/1941 | Small | |
| 2,350,818 A | 6/1944 | Rees | |
| 2,576,290 A | 11/1951 | Fisher, Jr. | |
| 2,612,456 A | 9/1952 | Thacker et al. | |
| 2,714,560 A | 8/1955 | Hookway | |
| 2,763,568 A | 9/1956 | McBride | |
| 3,506,474 A | 4/1970 | Neuhaus et al. | |
| 3,769,063 A | 10/1973 | Kizawa | |
| 3,829,323 A | 8/1974 | Krich | |
| 4,158,053 A | 6/1979 | Greene et al. | |
| 4,166,054 A | 8/1979 | Meeske et al. | |
| 4,812,336 A | 3/1989 | Okamoto et al. | |
| 5,266,322 A | 11/1993 | Myers et al. | |
| 5,601,876 A | 2/1997 | Oates et al. | |
| 5,607,665 A | 3/1997 | Calello et al. | |
| 5,668,494 A | 9/1997 | Nicollini et al. | |
| 5,766,332 A | 6/1998 | Graves et al. | |
| 5,792,447 A | 8/1998 | Socci et al. | |
| 5,817,304 A | 10/1998 | Mondet et al. | |
| 5,863,523 A | 1/1999 | Socci et al. | |
| 5,935,590 A | 8/1999 | Razzano | |
| 5,977,217 A | 11/1999 | Socci et al. | |
| 5,989,575 A | 11/1999 | Razzano | |
| 6,139,822 A | 10/2000 | Socci et al. | |
| 6,296,839 B1 * | 10/2001 | Ramin et al. | 424/61 |
| 6,440,403 B1 | 8/2002 | Razzano | |
| 7,645,444 B2 | 1/2010 | Malnou et al. | |
| 2009/0068131 A1 | 3/2009 | Malnou | |
| 2009/0126316 A1 * | 5/2009 | Ilekti et al. | 53/111 R |
| 2010/0003201 A1 | 1/2010 | Wahl | |

OTHER PUBLICATIONS

Deville, Gina, "Peek-A-Polish /OPI Black Spotted swatches, review & Application tips / EDIT: Ingredients list", Jun. 18, 2012, pp. 1-14, <http:!/peek-a-polish.blogspot.com/2012/06/opi-black-spotted-swatches-review.html>.
"Frazzle and Aniploish: OPI Black Spotted", Jul. 6, 2012.
"Special Effects—Top Coats", 2012.

* cited by examiner

*Primary Examiner* — Robert A Wax
*Assistant Examiner* — Randeep Singh
(74) *Attorney, Agent, or Firm* — Lerner, David, Littenberg, Krumholz & Mentlik, LLP

(57) ABSTRACT

An aqueous nail enamel composition of non-toxic components forms a decorative irregular film over natural or synthetic human nails. The nail enamel composition includes water, at least one film forming component, and at least one silicone component in a homogeneous mixture. The film forming component forms a decorative irregular film by containing a plurality of voids upon drying.

24 Claims, No Drawings

NAIL ENAMEL COMPOSITIONS HAVING DECORATIVE VOIDS

BACKGROUND OF THE INVENTION

The present invention relates in general to nail enamel compositions, and more particularly, to such compositions which are suitable for coating natural and synthetic nails. Still more particularly, the present invention relates to nail enamel compositions which produce a film having a decorative appearance.

Nail enamel compositions include a class of nail care products regularly used by women as part of their beauty care routine. These nail care products are available in a multitude of product formulations, from clears to infinite colors. Typically, clear nail enamel compositions include a film forming polymer, a film forming resin, a plasticizer and one or more solvents. In the case of a color nail enamel composition, the product may also include a thixotropic compound, a suspending agent and one or more pigments, or in the alternative, an organic coloring polymer may be used. In addition to these components, a number of optional and proprietary components are often included such as UV light absorbers, moisturizers, stabilizers, fragrances and the like.

Nail enamel compositions have heretofore been formulated to satisfy a number of highly desirable film forming properties. For example, desirable properties often include smoothness of application, rapid dry time, scratch resistance, detergent and oil resistance, lustrous appearance, wear and chip resistance and the like. Often most important, it has been highly desirable that the resulting nail enamel film be smooth and uninterrupted by imperfections, for example, orange peel effect, wrinkling, cracking, pitting, bubbling and the like. To this end, nail enamel compositions have included many different types of additives in order to improve the aforementioned desirable properties of the resulting film.

Despite the improved properties of the nail enamel film, the aesthetic or decorative appearance differed very little, except generally for color. Often, manufacturers would produce nail enamel compositions having the same popular colors as their competitors. This provided little distinction between nail enamel products of different manufacturers to the ultimate consumer. Nail enamel compositions having a more decorative appearance were produced by including small pieces of light reflecting decorative material known as glitters within the composition. From the foregoing, it can be appreciated that the appearance of nail enamel compositions have differed very little over the years. To this end, the present invention provides a nail enamel composition which produces a film having a textured decorative appearance heretofore unknown.

Paints and lacquers for furniture and home remodeling applications having an irregular film, for example, a wrinkle or crackle finish have been known for many years. For example, paints and lacquers having a crackle finish are known from Egelhoff, U.S. Pat. No. Re. 16,760; Neuhaus, U.S. Pat. No. 2,021,152; Rees, U.S. Pat. No. 2,350,818; Thacker, et al., U.S. Pat. No. 2,612,456; Hookway, U.S. Pat. No. 2,714,560; and Oates, et al., U.S. Pat. No. 5,601,876. Paints and lacquers having a wrinkle finish are known from Root, U.S. Pat. Nos. 1,689,892 and 1,732,661; Small, U.S. Pat. No. 2,248,254; Ficher, U.S. Pat. No. 2,576,290; McBride, U.S. Pat. No. 2,763,568; Neuhaus, et al., U.S. Pat. No. 3,506,474; Kirch, U.S. Pat. No. 3,829,323; and Okamoto, et al., U.S. Pat. No. 4,812,336. These known paints and lacquers are not suitable for human contact due to the inclusion of generally toxic compounds and those which are not approved by the FDA.

Despite these known paints and lacquers, there has generally been unknown any variety of nail enamel compositions containing non-toxic components which when applied to natural or synthetic nails will produce a film having a textured decorative appearance.

Socci et al., U.S. Pat. No. 6,139,822 discloses aqueous nail enamel compositions which form a decorative irregular film containing uniform or random cracks upon drying. For example, the '822 patent discloses irregular films having cracks in the nature of fissures or complete or partial splits, breaks or fine lines in the nail enamel film that produce, for example, slight or narrow spaces or voids, including hairline cracks and large voids. Like the '822 patent, the present invention discloses aqueous nail enamel compositions which produce irregular films which exhibit a decorative appearance by virtual forming a plurality of voids in a uniform, random or irregular pattern.

SUMMARY OF THE INVENTION

The present disclosure relates to an aqueous based decorative nail enamel composition for forming an irregular film containing voids over natural or synthetic nails, comprising water, at least one film forming component, and at least one silicone component present in a sufficient amount wherein voids form within the at least one film forming component upon drying of the nail enamel composition.

In another embodiment, an aqueous based nail decorative enamel composition for forming an irregular film containing voids over natural or synthetic nails, comprising water, at least one silicone component forming a homogeneous mixture with the water, at least one file forming component, and at least one color component wherein the at least one silicone component is present in a sufficient amount wherein a plurality of voids form in the at least one film forming component upon drying of the nail enamel composition.

In a further embodiment, an aqueous based decorative nail enamel composition for forming an irregular film containing voids over natural or synthetic nails upon drying, comprising water in an amount ranging from 30% to 50% by weight of the composition, at least one film forming component in an amount ranging from 15% to 30% by weight of the composition, at least one silicone component in an amount ranging from 0.5% to 10% by weight of the composition, and at least one color component, wherein the at least one silicone component is present in a sufficient amount wherein a plurality of voids form in the at least one film forming component upon drying of the nail enamel composition.

In yet another embodiment, a method of forming an irregular film containing voids over a base nail enamel composition applied to natural or synthetic nails, comprising applying a base nail enamel composition to natural or synthetic nails, applying an aqueous based nail enamel composition over the base nail enamel composition, the aqueous nail enamel composition comprising water, at least one silicone component, and at least one film forming component, wherein the at least one silicone component is present in a sufficient amount wherein a plurality of voids form in the at least one film forming component upon drying of the nail enamel composition.

DETAILED DESCRIPTION OF THE PREFERRED EMBODIMENTS

In describing the preferred embodiments of the subject matter to be described, specific terminology will be resorted to for the sake of clarity. However, the invention is not intended to be limited to the specific terms so selected, and is to be understood that each specific term includes all technical equivalence which operate in a similar manner to accomplish a similar purpose. Furthermore, any range of numbers recited in the specification referring to various aspects or embodiments of the invention, as well as in the claims hereinafter, such as that representing a particular set of properties, units of measure, conditions, physical states or percentages, is by way of example and is intended to literally incorporate expressly herein by reference or otherwise, any number falling within such range, including any subset of numbers or ranges subsumed within any range so recited.

The present invention broadly discloses nail enamel compositions which, when forming a film therefrom, will exhibit a decorative appearance by virtue of forming an irregular film. By irregular film, it is meant that the film will contain a plurality of voids, such as, by way of example, in a uniform, random or irregular pattern. The term void includes an opening of regular, irregular or random shape, as distinguished from cracks, fine lines or hairline cracks in the nail enamel film. A pseudovoid is also contemplated wherein a thinning of the nail enamel film occurs to produce the appearance of a void. The voids may be of uniform, random or irregular patterns formed over the natural or synthetic nail which are produced during drying of the nail enamel composition.

The voids may further have any uniform, random or irregular size or shape. For example, the voids may appear to have a circular, oval, polygonal, square, triangular, trapezoidal, or other geometric or irregular shape. In addition, the voids may have a non-uniform shape which cannot be characterized in terms of a known geometric or other shape. In this regard, the voids may be irregular in shape and not definable in terms of geometric or non-geometric shapes. It is therefore contemplated that the nail enamel compositions will produce films having voids of multiple sizes and multiple shapes, both uniformly and/or randomly and/or irregularly dispersed throughout the dried film to produce a decorative appearance.

The nail enamel compositions of the present invention which produce an irregular film including voids are applied to natural or synthetic nails which may have been previously coated with a base nail enamel composition which are solvent or aqueous based. By aqueous based it is meant that the film forming polymers and/or copolymers in the composition are soluble in or form a dispersion or emulsion with water. The primary solvent or diluent in the aqueous based compositions are therefore water, although lesser amounts of organic solvents may be present, preferably in small amounts compared to the amount of water in the composition. For example, small amounts of organic solvents may enter the aqueous based compositions through the inclusion of other components such as in suspending agent dispersions and coalescing solvents It is contemplated that two nail enamel coating systems can be produced for creating an irregular film in accordance with the present invention. These systems are classified as to whether the base nail enamel composition is based upon an organic solvent or an aqueous medium. Specifically, the two systems include (1) an aqueous base coat composition for receiving an aqueous decorative top coat composition which forms an irregular film, and (2) a solvent base coat composition for receiving an aqueous decorative top coat composition which forms an irregular film. For purposes of the present application, a base nail enamel composition or base composition will refer to the composition which is applied directly to the natural or synthetic nail. On the other hand, a decorative nail enamel composition or decorative composition refers to the nail enamel composition which forms the irregular film having voids pursuant to the present invention.

Solvent base coat compositions can be formulated as a clear or color nail enamel composition which is suitable for coating natural and synthetic nails. Typically, a clear nail enamel composition contains one or more film forming components, a plasticizer and one or more solvents. In the case of a color base coat nail enamel composition, the composition may include a thixotropic compound, a suspending agent and one or more pigments, or in the alternative, an organic coloring polymer may be used. In addition to these compounds, a number of optionally and proprietary components may be included such as UV light absorbers, moisturizers, stabilizers, fragrances and the like. Suitable solvent base coat nail enamel compositions are disclosed in U.S. Pat. No. 5,977,217, entitled Quick Drying Nail Enamel Composition, filed on Apr. 7, 1998 in the name of Socci, et al.; U.S. Pat. No. 5,863,523, entitled Nail Enamel Composition, filed on Dec. 10, 1996 in the name of Socci, et al.; and U.S. Pat. No. 5,792,447, entitled Nail Enamel Composition, filed on Nov. 15, 1996 in the name of Socci, et al., which patents are assigned to the same assignee of the present application, the disclosures of which are incorporated herein by reference.

The solvent base coat nail enamel compositions may contain one or more film forming components such as film forming polymers, for example, cellulose acetate, cellulose acetate butyrate, ethyl cellulose, vinyl polymers, nitrocellulose, as well as methacrylate and acrylate type polymers, and mixtures thereof. Nitrocellulose provides an unusual combination of properties of toughness, durability, solubility and solvent release. Examples of nitrocellulose are the so called nitrocellulose RS ⅛ sec. and ½ sec.; nitrocellulose RS ½ sec.; and nitrocellulose RS 5-6 sec. and 60-80 sec., which have higher viscosities than the earlier grades. The term "RS" refers to the brand of nitrocellulose with a nitrogen content of about 11.2-12.8% with solubility in esters, ketones and glycol ethers manufactured by Hercules, Inc. The terms ⅛ sec., ½ sec., ½ sec., 5-6 sec., etc. represent viscosity and refer to the time it takes for a ball to fall to a given depth in the material. Nitrocellulose is typically supplied in 70% concentrations, wet with 30% ethyl or isopropyl alcohol. As used in the present application, the percentage of nitrocellulose in a given composition will be on a wet basis unless otherwise stated. Nail enamel compositions may include the above film forming polymers and combinations thereof in an amount ranging from about 5 to 25% by weight, and more preferably in the range of about 10 to 15% by weight.

In addition to the aforementioned film forming polymers, the solvent base coat nail enamel compositions can also include one or more film forming resins. Exemplary film forming resins which may be used either alone or in combination with the film forming polymers include, for example, drying and non-drying alkyd resins, polyvinyl resins for example polyvinyl acetate, polyester resins, epoxy resins, acrylic polymers and copolymers, maleic modified glycerol esters of rosin, and toluene sulfonamide/epoxy resins, e.g., tosylamide epoxy resin. It is also within the scope of the solvent base coat compositions to include aldehyde condensation products such as arylsulfonamide formaldehyde resins, specifically toluene sulfonamide formaldehyde resin which is a condensation product of formaldehyde and toluene sulfonamide. The amount of film forming resin and combinations thereof can range from about 2 to 25% by weight of the composition, and preferably about 7 to 12% by weight of the composition. Overall, the solvent base coat nail enamel composition can include a number of film forming components in the overall range of from about 2 to 25% by weight of the composition, and preferably about 10 to 15% by weight of the composition.

In addition to the film forming components, the solvent base coat nail enamel compositions may include at least one plasticizer to soften and plasticize particularly the film forming polymer. The plasticizer may be in either liquid or solid form, as well as combinations thereof. The solvent base coat compositions may include one or more of the known plasticizers which are suitable for use in nail enamel compositions. Examples of such known plasticizers include tricresyl phosphate, dibutyl tartrate, benzyl benzoate, tributyl phosphate, butyl acetyl ricinoleate, butyl glycolate, butyl stearate, triphenyl phosphate, triethyl citrate, camphor, castor oil, esters of citric, stearate, phalic, oleic, phosphate, butyric and benzoic acid, glyceryl triacetate and glyceryl triproprionate, 2,2,4-trimethyl-1,3-pentandiiol diisobutyrate and mixtures thereof. The solvent base coat nail enamel compositions also contemplate the use of phthalate type plasticizers either alone or in combination with the aforementioned plasticizers, for example, diamylphthalate, dibutyl phthalate, diethyl phthalate, dioctyl phthalate, dibutoxy ethylphthalate and mixtures thereof.

Plasticizers included in the solvent base coat compositions are in amounts sufficient to provide acceptable flexibility to the nail enamel film on the human or synthetic nail surface. In this regard, the amount of plasticizer and combinations thereof for use in the solvent base coat compositions range from about 1 to 20% by weight, and preferably about 5 to 10% by weight.

The solvent base coat nail enamel compositions may also include one or more organic solvents such as those generally used in conventional nail enamel compositions. Examples of these solvents include ethyl acetate, methyl acetate, ethanol, isopropanol, propyl acetate, n-butanol, xylene, DI acetone alcohol, aromatic (containing phenyl groups), amyl acetate, ethers, ketones, alkanes for example, pentane, cyclopentane, hexane, toluene, heptane, cyclohexane, cyclic ethers for example, tetrahydrofuran and 1,4-dioxane, cellosolve, butyl cellosolve acetate, cellosolve acetate, methyl cellosolve acetate, butyl cellosolve, ethyl cellosolve, phenylated solvents for example, xylene, esters of acetic acid for example, methyl acetate, ethyl acetate, n-butyl acetate, chlorinated hydrocarbons for example, methylene chloride, chloroform and methylchloroform. The aforementioned solvents can be used alone or in mixtures thereof. In general, the amount of solvent used in the compositions range from about 60 to 80% by weight, and preferably about 65 to 75% by weight.

In color solvent base coat compositions, one or more pigments and a suspending agent may also be added. One or more known organic colorants which are well known in the nail enamel art may also be added to these compositions. Pigments are added to the composition to provide cosmetically acceptable shades and to pacify the films. Pigments may include any of those pigments which are generally known for use in nail enamel compositions. For example, these pigments can include cosmetic grade or purified titanium dioxide, black iron oxide, black #2, yellow and red iron oxides, bismuth oxychloride, iron blue, iron black, mica particles, ultramarine blue, D&C Red #7, chromide oxide greens, carbon black, lampblack and the like. Other pigments which may be used in the compositions may include the Lake pigments, for example, D&C Red #6 barium Lake, D&C Red #7 calcium Lake and the like.

In addition to the above named pigments, there may also be included titanated micas, polyethylene teraphthalates and pearl essence which is a suspension of crystalline guanine in nitrocellulose and solvents, as well as other additives which will affect the appearance of the pigment. Although the amount of pigment in the compositions will vary as a function of the type of pigment and other components included in the composition, in general, pigments can be included in an amount up to about 10% by weight of the nail enamel composition.

When pigments are included in compositions, it is useful to include a suspending agent for enhancing the suspension of the pigments in the other components of the solvent base coat composition. Although a number of suspending agents which are generally used in conventional nail enamel compositions may be used, preferred suspending agents include colloidal clays, montmorillonite clays, especially stearalkonium hectorite, stearalkonium bentonite, fumed silica, and mixtures thereof. The suspending agent is present in the compositions in amounts sufficient to produce a gel, preferably a colloidal gel. In general, the suspending agent is included in the amount ranging from about 0.5 to 5% by weight of the solvent base coat nail enamel composition.

In addition to the above described components, the solvent base coat compositions may also include additional additives including stabilizers, thixotropic agents, UV light absorbers such as ectocrylene and benzophenone-1, fragrances, moisturizers and medicants, depending on the intended result. These components are well known in the art and may be included in amounts well within the teachings of the prior art.

The solvent base coat nail enamel compositions can be manufactured by thoroughly and intimately mixing together all the components in the amounts described. Examples of satisfactory equipment and how to use then are readily apparent to one of ordinary skill in the nail enamel art.

The following examples illustrate solvent base coat nail enamel compositions suitable for use with the aqueous decorative compositions of the present invention. These examples are by way of illustration and are not intended to be limiting the present invention either as to the inclusion of a greater or lesser number of components, the substitution of additional or other components or variations in the percentages of the range of components.

Example 1

|  | WT/PERCENT |
|---|---|
| ETHYL ACETATE | 43.60 |
| BUTYL ACETATE | 12.40 |
| NITROCELLULOSE | 12.00 |
| ISOPROPYL ALCOHOL | 5.50 |
| TOSYLAMIDE EPOXY RESIN | 6.50 |
| SUCROSE ACETATE ISOBUTYRATE | 5.00 |
| R779 ACRYLATES COPOLYMER | 3.75 |
| TRIPHENYL PHOSPHATE | 3.75 |
| POLYESTER RESIN | 0.75 |
| DIBUTYL PHTHALATE | 0.50 |
| DIACETONE ALCOHOL | 0.50 |
| BENZOPHENONE 1 | 0.10 |
| POLYETHER MODIFIED DIMETHYLPOLYSILOXANE | 0.50 |
| DIMETHICONE | 0.20 |
| STEARALKONIUM HECTORITE | 1.00 |
| TITANIUM DIOXIDE | 1.00 |
| D&C RED #6 CALCIUM LAKE | .75 |
| RED IRON OXIDE | 1.00 |
| BLACK IRON OXIDE | .20 |
| MICA | 1.00 |

Example 2

|  | WT/PERCENT |
|---|---|
| ETHYL ACETATE | 37.01 |
| BUTYL ACETATE | 14.20 |
| NITROCELLULOSE | 12.80 |
| ISOPROPYL ALCOHOL | 6.40 |
| TOSYLAMIDE EPOXY RESIN | 6.60 |
| SUCROSE ACETATE ISOBUTYRATE | 5.90 |
| ACRYLATES COPOLYMER | 0.70 |
| TRIPHENYL PHOSPHATE | 2.70 |
| POLYESTER RESIN | 1.20 |
| DIBUTYL PHTHALATE | 0.90 |
| CAMPHOR | 0.10 |
| HEPTANE | 0.30 |
| PROPYL ACETATE | 0.20 |
| STEARALKONIUM HECTORITE | 0.10 |
| STEARALKONIUM BENTONITE | 1.10 |
| DIACETONE ALCOHOL | 0.70 |
| BENZOPHENONE 1 | 0.30 |
| POLYETHER MODIFIED DIMETHYLPOLYSILOXANE | 0.40 |
| ETOCRYLENE | 0.05 |
| DIMETHICONE | 0.10 |
| TITANIUM DIOXIDE | 0.20 |
| FD&C YELLOW #5 ALUMINUM LAKE | 1.00 |
| FERRIC AMMONIUM FERROCYANIDE | 0.04 |
| MICA | 7.00 |

Example 3

|  | WT/PERCENT |
|---|---|
| ETHYL ACETATE | 41.20 |
| BUTYL ACETATE | 15.80 |
| NITROCELLULOSE | 11.50 |
| ISOPROPYL ALCOHOL | 6.40 |
| TOSYLAMIDE EPOXY RESIN | 6.60 |
| SUCROSE ACETATE ISOBUTYRATE | 5.90 |
| ACRYLATES COPOLYMER | 0.70 |
| TRIPHENYL PHOSPHATE | 2.90 |
| POLYESTER RESIN | 0.60 |
| DIBUTYL PHTHALATE | 1.70 |
| CAMPHOR | 0.20 |
| HEPTANE | 0.50 |
| PROPYL ACETATE | 0.50 |
| STEARALKONIUM HECTORITE | 0.10 |
| STEARALKONIUM BENTONITE | 0.80 |
| DIACETONE ALCOHOL | 0.50 |
| BENZOPHENONE 1 | 0.05 |
| POLYETHER MODIFIED DIMETHYL POLYSILOXANE | 0.40 |
| ETOCRYLENE | 0.05 |
| DIMETHICONE | 0.10 |
| TITANIUM DIOXIDE | 2.00 |
| FD&C YELLOW #5 ALUMINUM LAKE | 0.10 |
| RED IRON OXIDE | 0.10 |
| BLACK IRON OXIDE | 1.30 |

Example 4

|  | WT/PERCENT |
|---|---|
| POLYESTER RESIN | 8.40 |
| TOSYLAMIDE EPOXY RESIN | 4.96 |
| NITROCELLULOSE 1/4/5-6 sec. | 8.87 (dry) |
| ETHYL ACETATE | 30.00 |
| BUTYL ACETATE | 27.18 |
| ISOPROPYL ALCOHOL | 11.22 |
| TRIPHENYL PHOSPHATE | 4.62 |
| 2,2,4-TRIMETHYL-1,3-PENTANEDIOL DIISOBUTYRATE | .85 |
| DIBUTYL PHTHALATE | .50 |
| CAMPHOR | .10 |
| DIACETONE ALCOHOL | .68 |
| CITRIC ACID | 0.02 |
| STEARALKONIUM HECTORITE | .25 |
| STEARALKONIUM BENTONITE | .78 |
| D & C RED #6 BARIUM LAKE | .90 |
| D & C RED #7 CALCIUM LAKE | .35 |
| TITANIUM DIOXIDE | .32 |

Example 5

|  | WT/PERCENT |
|---|---|
| NITROCELLULOSE 1/4/1/2 sec. | 12.52 (dry) |
| TOLUENE SULFONAMIDE FORMALDEHYDE RESIN | 8.12 |
| BUTYL ACETATE | 22.79 |
| ETHYL ACETATE | 18.74 |
| TOLUENE | 19.69 |
| ISOPROPYL ALCOHOL | 5.72 |
| CAMPHOR | 1.10 |
| BENZOPHENONE 1 | 0.04 |
| DIBUTYL PHTHALATE | 5.92 |
| DIACETONE ALCOHOL | .84 |
| STEARALKONIUM HECTORITE | .05 |
| STEARALKONIUM BENTONITE | 1.24 |
| CITRIC ACID | 0.02 |
| POLYESTER RESIN | 1.07 |
| TOLUENE SULFONAMIDE EPOXY | 0.15 |
| TITANIUM DIOXIDE | .33 |
| D & C RED #6 BARIUM LAKE | .90 |
| D & C RED #7 CALCIUM LAKE | .76 |

Example 6

|  | WT/PERCENT |
|---|---|
| POLYESTER RESIN | 5.60 |
| TOSYLAMIDE EPOXY RESIN | 4.95 |
| NITROCELLULOSE 1/4/5-6 sec. | 8.85 (dry) |
| ETHYL ACETATE | 32.50 |
| BUTYL ACETATE | 26.50 |
| ISOPROPYL ALCOHOL | 11.50 |
| TRIPHENYL PHOSPHATE | 4.65 |
| 2,2,4-TRIMETHYL-1,3-PENTANEDIOL DIISOBUTYRATE | .92 |
| DIBUTYL PHTHALATE | .50 |
| CAMPHOR | .10 |
| DIACETONE ALCOHOL | .68 |
| CITRIC ACID | 0.02 |
| STEARALKONIUM HECTORITE | .25 |
| STEARALKONIUM BENTONITE | .75 |
| TITANIUM DIOXIDE | 1.16 |
| IRON OXIDES | .27 |
| D & C RED #7 | .20 |
| ETOCRYLENE | .50 |
| MICA | .10 |

Example 7

| | WT/PERCENT |
|---|---|
| NITROCELLULOSE 1/4/1/2 sec. | 12.57 (dry) |
| POLYESTER RESIN | 8.10 |
| TOLUENSULFONAMIDE EPOXY RESIN | .35 |
| ETHYL ACETATE | 30.39 |
| BUTYL ACETATE | 16.75 |
| BUTYL ALCOHOL | 1.71 |
| PROPYL ACETATE | 9.44 |
| ISOPROPYL ALCOHOL | 9.74 |
| DIBUTYL PHTHALATE | 6.19 |
| CAMPHOR | 1.10 |
| DIACETONE ALCOHOL | .66 |
| STEARALKONIUM BENTONITE | 1.01 |
| STEARALKONIUM HECTORITE | .02 |
| ETOCRYLENE | .50 |
| BENZOPHENONE 1 | 0.08 |
| CITRIC ACID | 0.02 |
| TITANATED MICA | 0.12 |
| TITANIUM DIOXIDE | 1.00 |
| D & C RED #6 BARIUM LAKE | .05 |
| IRON OXIDES | .10 |
| D & C RED #7 CALCIUM LAKE | .10 |

The aqueous based decorative nail enamel compositions which form an irregular film containing voids may include one or more aqueous emulsion or dispersion polymers which include copolymers which are suitable for forming an adherent film to a natural or synthetic nail. By aqueous based it is meant that the film forming polymers and/or copolymers in the composition are soluble in or form a dispersion or emulsion with water. The primary solvent or diluent in the aqueous based compositions are therefore water, although lesser amounts of organic solvents may be present, preferably in small amounts compared to the amount of water in the composition. For example, small amounts of organic solvents may enter the aqueous based compositions through the inclusion of other components such as in suspending agent dispersions and coalescing solvents.

By way of example, these aqueous polymers include the general class of acrylic polymers, such as styrenated acrylic polymers capable of forming colloidal dispersions and emulsions, polyurethane and polyurethane copolymers, vinyl acetate polymers and copolymers, olefin polymers and copolymers. Other contemplated aqueous polymers are disclosed in Myers, et al., U.S. Pat. No. 5,266,322 which discloses a first aqueous emulsion containing a sulfopolyester and a copolymer of vinyl acetate and dialkyl maleate and a second aqueous emulsion which contains acetoacetoxy-ethyl alkylacrylate, or the reaction product of acetoacetoxy-ethyl alkylacrylate with a vinyl functional monomer; and Green, et al., U.S. Pat. No. 4,158,053 which discloses aqueous emulsion copolymers having a solid content of from about 30-55%, which is prepared by the polymerization of two or more specific types of disclosed monomers. The polymers and copolymers disclosed in Myers, et al. and Green, et al. are incorporated herein by reference.

By way of example, styrenated acrylic emulsion polymers suitable for use in an aqueous base coat nail enamel composition are obtainable from S.C. Johnson Polymer, a division of S.C. Johnson Commercial Markets, Inc. of Sturtebant, Wis. under the marks Joncryl 1907, Joncryl 1908 and Joncryl 2561. Joncryl 1907 is supplied as an emulsion containing 46% non volatiles by weight, and a viscosity of 500 cps. Joncryl 1908 is supplied as an emulsion containing 48% by weight non volatiles having a viscosity of 500 cps and Joncryl 2561 is supplied as an emulsion containing 48% by weight non volatiles having a viscosity of 700 cps.

Additional aqueous acrylic emulsion polymers are Joncryl 530 which is an emulsion polymer having 49% by weight non-volatiles, Joncryl 95 which is a colloidal polymer dispersion having a non-volatile content of 30% by weight, Joncryl SCX-1532 which is an emulsion polymer having 51% by weight non-volatiles, Joncryl SCX-2500 which is an emulsion polymer having 43% by weight non-volatiles, Joncryl 538 which is an emulsion polymer having 45% by weight non-volatiles and Joncryl SCX 1970 which is an emulsion polymer having 48% by weight non-volatiles, the aforementioned aqueous polymers being available from S.E. Johnson Polymer. In addition, aliphatic waterborne urethane polymers such as Sancure 1073C which is available from B.F. Goodrich Specialty Chemicals of Cleveland, Ohio is also suitable for use in an aqueous decorative nail enamel composition. Sancure 1073C has a 30% non-volatiles content at a sward hardness of 100.

From the foregoing, it should be appreciated that a large number of aqueous emulsion and colloidal dispersion polymers and copolymers are suitable for use in the aqueous decorative nail enamel compositions in accordance with the present invention, and accordingly, are not limited to only those described herein.

The aqueous decorative nail enamel compositions of the present invention may include any number of aqueous polymers, copolymers, and combinations thereof, in an amount ranging from about 15 to 30% by weight, and more preferably, in the range of about 18 to 25% by weight of the composition by way of example.

In addition to the aforementioned aqueous polymers, the aqueous decorative nail enamel compositions may include one or more coalescing solvents which facilitates the aqueous polymer to form a continuous polymer film. Exemplary coalescing solvents which may be used in the present invention either alone or in combination include, for example, glycol ethers, such as ethylene glycol monobutyl ether, diethylene glycol monomethyl ether, propylene glycol monomethyl ether, dipropylene glycol monomethyl ether, isopropyl alcohol, butyl carbitol, ethylene glycol 2-ethyl hexyl ether, ethylene glycol phenyl ether, diethylene glycol monopropyl ether, diethylene glycol monohexyl ether, diethylene glycol monobutyl, propylene glycol monopropyl ether, propylene glycol tertiary butyl ether, dipropylene glycol monopropyl ether, dipropylene glycol tertiary butyl ether, dipropylene glycol monobutyl ether, tripropylene glycol methyl ether, aromatic based glycol ether, 2,2,4-trimethyl-1,3-pentanediol monoisobutyrate, benzyl alcohol, n-methylpyrolidone, diacetone alcohol, exxate 700, exxate 800, exxate 900, exxate 1000, exxate 1300 and mixtures thereof. The aqueous decorative compositions may include coalescing solvents and combinations thereof in an amount ranging from about 1 to 8% by weight, and more preferably, in the range of about 2 to 4% by weight of the composition by way of example.

The aqueous decorative nail enamel compositions of the present invention may also include co-solvents such as isopropyl alcohol, ethyl alcohol, methanol, diacetone alcohol and mixtures thereof. The co-solvents can be used to control the solid content of the composition and the resulting irregular film, as well as increasing the drying rate of the aqueous decorative nail enamel composition when forming an irregular film. Further, the co-solvents will also protect the aqueous decorative compositions against potential freezing during shipping and storage.

It may be desirable to provide color to the aqueous decorative nail enamel composition. In this regard, any one of well-known colorants may be employed. For example, organic and inorganic pigments, as well as organic colorants such as tints or dyes may be used as is well known in the nail enamel art, such as those noted hereinabove. When pigments are employed, a suspending agent such as those previously noted may be employed to assist in the suspension of the pigments. In addition, acrylic copolymer aqueous dispersions may also be used as a suspending agent. One such acrylic copolymer is known as Drewthix 53L which is obtained from Drew Industrial of Boonton, N.J. which is a division of Ashland Chemical Company.

Suitable pigments, by way of one example only, are available as an aqueous dispersion containing styrene acrylic resin from Sun Chemical Corporation of Cincinnati, Ohio. Organic colors referred to as tints are available from Penn Color of Doylestown, Pa. The pigments may be introduced into the aqueous decorative compositions in the form of an aqueous dispersion, which in addition to the pigments may include other components. These components may include, for example, a film former such as acrylates/ethyhexyl acrylate copolymer, water, a pH adjuster and preservatives.

In addition, suspending agents as noted herein, such as silica and silica dispersions, may be used to prevent separation and settling of pigmented aqueous decorative compositions. By way of example, one such aqueous silica dispersion in addition to containing silica as the suspension agent, may include styrene/acrylates copolymers as a film former, ammonium hydroxide as a pH adjuster, and water, propylene glycol and butyl alcohol as solvents.

The aqueous decorative compositions may also include additional additives, including dispersing agents, wetting agents, thickeners, fragrances, anti-foams, buffers, plasticizers, chelating agents, anti-freezing agents, UV light absorbing agents, stabilizers, fillers, etc. The selection of these optional ingredients is well within the skill of those familiar with the nail enamel art.

The formation of voids in the aqueous decorative nail enamel compositions is, by way of contemplated explanation, a result of the presence of at least one silicone component in the composition which is generally not miscible in water. However, it is contemplated that silicone compounds that one soluable in water might also be suitable for use in the compositions. By way of example, one class of known silicone compounds which may be suitable for use in aqueous the decorative compositions are those generally known for their anti-foaming properties. Exemplary silicone compounds which may be used in the aqueous decorative composition, either alone or in combination, include, Xiameter® ACP-000-FG which is a compounded silicone fluid (CAS Number 556-67-2 "Octamethylcylotetrasiloxane"; CAS Number 63148-62-9 "Polydimethylsiloxane"; CAS Number 67762-90-7 "Methylated Silica"; CAS Number 541-02-6 "Decamethylcyclopentasiloxane"; and "Dimethylsiloxane"); and Dow Corning 163® Additive which is a compounded Silicone fluid (CAS Number 70131-67-8 "Dimethyl Siloxane, hydroxy-terminated"; CAS Number 63148-62-9 "Polydimethylsiloxane"; and CAS Number 67762-90-7 "Methylated Silica"), both available from Dow Corning Corporation of Midland, Mich.

Other contemplated Silicone compounds for using in the aqueous compositions include SF96-1000 which is a silicone compounded fluid (CAS number 63148-62-9 "polydimethylsiloxane") available from Momentive of Columbus, Ohio; Dow Corning 200® which is a silicone compounded fluid (CAS Number 107-46-0 "Hexamethyldisiloxane" available from Dow Corning; and Ultrapure® Dimethiconol 70 which is a silicone compounded fluid (CAS Number 70131-67-8 "Polydimethylsiloxane, Hydroxyl Dimethyl terminated") available from Ultra Chemical of Red Bank, N.J. Although the disclosed silicone compounds may include a mixture of silicone compounds, it is contemplated that the addition of a single silicone compound to the aqueous composition will produce voids, and is therefore within the scope of the present invention.

The silicone component, which may include a single silicone compound or a mixture of silicone compounds, is present in the aqueous decorative composition in a sufficient amount wherein a plurality of voids form in the film forming component upon drying of the nail enamel composition. For example, it is contemplated that the aqueous decorative compositions of the present invention may include the silicone components and combinations thereof in an amount ranging from about 0.5-10% by weight, preferably, in the range of about 2-4% by weight, and more preferably, in the range of about 2-3% by weight of the composition by way of example.

The aqueous decorative nail enamel compositions in accordance with the present invention can be manufactured in a similar manner as previously noted by homogeneously mixing together all of the components in the amounts described in accordance with the present invention. The following examples are provided to illustrate suitable aqueous decorative compositions which are capable of forming a continuous film at room temperature having voids. These examples are by way of illustration and are not intended to be limiting of the present invention either as to the inclusion of a greater or lesser number of components, the substitution of additional or other components or variations in the percentages of the range of components.

Example 8

|  | WT/PERCENT |
|---|---|
| AQUEOUS POLYMERS/COPOLYMERS | 15 to 30 |
| SUSPENSION COMPONENT | 0.1 to 5 |
| COLOR COMPONENT | 0.1 to 5 |
| SILICONE COMPONENT | 0.5 to 10 |
| (WATER IN COMPOSITION) | (30 to 50) |

Example 9

|  | WT/PERCENT |
|---|---|
| AQUEOUS POLYMERS/COPOLYMERS | 18 to 25 |
| SUSPENSION COMPONENT | 0.75 to 1.5 |
| COLOR COMPONENT | 0.5 to 2 |
| SILICONE COMPONENT | 2 to 4 |
| (WATER IN COMPOSITION) | (35 to 40) |

Example 10

|  | WT/PERCENT |
|---|---|
| JONCRYL 1907 (20% water in composition) | 38.50 |
| JONCRYL 1908 (4.28% water in composition) | 8.60 |
| SILICA DISPERSION (13.3% water in composition) | 30.00 |
| BLACK IRON OXIDE DISPERSION (8.56% water in composition) | 18.00 |

-continued

| | WT/PERCENT |
|---|---|
| XIAMETER ® | 2.00 |
| DIACETONE ALCOHOL | 2.00 |
| ACETYL TRIBUTYL CITRATE | 0.90 |
| (WATER) | (46.00) |

Example 11

| | WT/PERCENT |
|---|---|
| JONCRYL 1907 (20% water in composition) | 38.50 |
| JONCRYL 1908 (4.28% water in composition) | 8.60 |
| SILICA DISPERSION (13.3% water in composition) | 30.00 |
| BLACK IRON OXIDE DISPERSION (8.56% water in composition) | 18.00 |
| DOW CORNING 163 ® | 2.00 |
| DIACETONE ALCOHOL | 2.00 |
| ACETYL TRIBUTYL CITRATE | 0.90 |
| (WATER) | (46.00) |

It is also contemplated that suitable aqueous decorative nail enamel compositions pursuant to the present invention can include the aforementioned aqueous polymers and copolymers without additional additives. That is, it is contemplated that the aqueous decorative compositions may comprise an aqueous emulsion or colloidal dispersion of the aforementioned polymers and copolymers having a silicone component to provide an irregular film forming voids upon application over natural or synthetic nails which may have applied thereto an aqueous or solvent base coat nail enamel composition.

In accordance with one embodiment, natural or synthetic nails may be initially coated with an aqueous base coat nail enamel composition which forms a continuous or uniform film over the underlying natural or synthetic nail. Suitable aqueous base coat nail enamel compositions are of the type disclosed in Socci et al., U.S. Pat. No. 6,139,822, the disclosure of which is incorporated herein by reference. In addition, it is contemplated that the aforementioned aqueous decorative nail enamel compositions which are formulated without a silicone component may also be used as a base coat composition. Other suitable aqueous base coat enamel compositions are disclosed in Greene et al., U.S. Pat. No. 4,158,053, the disclosure of which is disclosed herein by reference.

By way of example, aqueous base coat nail enamel compositions for application over natural or synthetic nails may include one or more of the aforementioned aqueous polymers and copolymers. In particular, by way of example only, suitable aqueous polymers include those referred to as acrylic polymers, styrenated acrylic polymers, acrylic-urethane polymers, vinyl acrylates, in addition to those mentioned hereinabove with respect to the aqueous decorative nail enamel compositions, and mixtures thereof.

The following examples are provided to illustrate aqueous base coat nail enamel compositions suitable for use with the aqueous decorative compositions of the present invention. These examples are by way of illustration and are not intended to be limiting of the present invention either as to the inclusion of a greater or lesser number of components, the substitution of additional or other components or variations in the percentages of the range of components. Example 12 provides a colorless aqueous base composition, while Examples 13 and 14 provide aqueous color nail enamel compositions.

Example 12

| | WT/PERCENT |
|---|---|
| JONCRYL 1908 | 67.00 |
| JONCRYL 1907 | 20.00 |
| ISOPROPYL ALCOHOL | 3.50 |
| TERTIARY BUTYL ETHER PROPYLENE GLYCOL | 3.00 |
| DIBUTYL PHTHALATE | 3.50 |
| WATER | 3.00 |

Example 13

| | WT/PERCENT |
|---|---|
| COMPOSITION OF EXAMPLE 8 | 97.08 |
| PIGMENT DISPERSIONS: WATER/STYRENE-ACRYLIC RESIN | 2.92 |

Example 14

| | WT/PERCENT |
|---|---|
| JONCRYL 1907 | 90.00 |
| TERTIARY BUTYL ETHER PROPYLENE GLYCOL | 4.2 |
| ISOPROPYL ALCOHOL | 2.5 |
| PENN COLOR SOLUTION 365282 | 3.3 |

The aqueous decorative nail enamel compositions of the present invention produce an irregular film containing voids when applied to a natural synthetic nail which may have been previously coated with a solvent or aqueous base nail enamel composition. As previously noted, the nail enamel composition systems of the present invention which provide an irregular film may include two combinations of solvent systems. Specifically, the two systems include (1) an aqueous base coat composition for receiving an aqueous decorative top coat composition which forms an irregular film, and (2) a solvent base coat composition for receiving an aqueous top coat composition which forms an irregular film. However, it is also contemplated that the aqueous decorative nail enamel compositions can be applied directly over the natural or synthetic nails. In this case, the color of the underlying natural or synthetic nail will be exposed by the voids providing a decorative effect. Applying the aqueous decorative compositions over natural or synthetic nails includes either over a base nail enamel composition or onto uncoated natural or synthetic nails or coated synthetic nails.

Initially, a natural or synthetic nail is optionally coated with either a solvent or aqueous base coat nail enamel composition. The base coat nail enamel composition is preferably allowed to partially dry, for example, to a condition known as "dry to touch." This condition arises when the surface of the resulting film may be touched with one's finger without leaving an impression of one's fingerprints. However, the film has yet to become completely dry. The time period to achieve a dry to touch will depend upon the particular base coat nail enamel composition being used, the thickness of the coat applied, temperature and humidity conditions. Once the base coat nail enamel composition has partially dried, the aqueous decorative nail enamel composition is applied thereover, preferably as a single coat. However, multiple coats may also be applied if so desired. As the decorative nail enamel composition dries, an irregular film will be formed by virtue of the presence of a plurality of voids. These voids may be small, as well as large, and produced in a random, irregular or more uniform pattern. The voids may be separated or partially or wholly connected. The voids allow the color of the underlying base coat composition or natural nail to show through providing a decorative pattern encompassed by the irregular film.

It is preferred that the base coat nail enamel composition not be completely dry, i.e., only dry to touch. Under these conditions, it is contemplated that the aqueous decorative nail enamel composition will strongly adhere to the base coat composition as the compositions completely dry. It has been found that if the base coat composition is initially completely dry, there is the possibility that the decorative nail enamel composition will have poor adherence. In any event, it is contemplated that a clear protective top coat, either aqueous or solvent based, can be applied to protect the aqueous decorative nail enamel composition. The protective top coat may also be tinted if so desired. To this end, there is known from the nail enamel art, as well as the examples disclosed herein, protective clear or tinted top coats which will form a protective continuous film.

Although the invention herein has been described with reference to particular embodiments, it is to be understood that the embodiments are merely illustrative of the principles and application of the present invention. It is therefore to be understood that numerous modifications may be made to the embodiments and that other arrangements may be devised without departing from the spirit and scope of the present invention as defined by the claims.

The invention claimed is:

1. An aqueous based decorative nail enamel composition for forming an irregular film containing voids over natural or synthetic nails or a polymer film forming base coat, said voids comprising an opening within the film having a regular, irregular or random shape, the composition comprising:
    water;
    at least one film forming component; and
    at least one silicone polymer present in a sufficient amount wherein voids form within the at least one film forming component upon drying of the nail enamel composition in a uniform, random or irregular pattern, where the at least one silicone polymer is present in the nail enamel composition in the amount of 0.5 to 10% by weight, wherein the voids expose therethrough a portion of the natural or synthetic nails or polymer film forming base coat.

2. The composition of claim 1, wherein the film forming component is selected from the group consisting of acrylic polymers, styrenated acrylic polymers, acrylic-urethane polymers, vinyl acrylates, polyurethane, polyurethane copolymers, vinyl acetate polymers and vinyl acetate copolymers, olefin polymers and olefin copolymers, and mixtures thereof.

3. The composition of claim 1, wherein the water and the at least one silicone polymer form a homogeneous mixture.

4. The composition of claim 1, wherein the at least one silicone polymer is present in the nail enamel composition in the amount of 2 to 4% by weight.

5. The composition of claim 1, further including at least one color component.

6. The composition of claim 5, further including a plurality of film forming components.

7. The composition of claim 6, further including a plurality of silicone polymers.

8. The composition of claim 1, wherein the at least one silicone polymer is selected from the group consisting of Octamethylcylotetrasiloxane, Polydimethylsiloxane, Methylated Silica, Decamethylcyclopentasiloxane, Dimethylsiloxane, Dimethyl Siloxane, hydroxy-terminated, Hexamethyldisiloxane, Hydroxyl Dimethyl terminated, and mixtures thereof.

9. The composition of claim 1, wherein water is present in the nail enamel composition in the amount of 30% to 50% by weight.

10. An aqueous based nail decorative enamel composition for forming an irregular film containing voids over natural or synthetic nails or a polymer film forming base coat applied thereto, said voids comprising an opening within the film having a regular, irregular or random shape, the composition comprising:
    water;
    at least one silicone polymer forming a homogeneous mixture with the water;
    at least one film forming component; and
    at least one color component;
    wherein the at least one silicone polymer is present in a sufficient amount wherein a plurality of voids form in a uniform, random or irregular pattern in the at least one film forming component upon drying of the nail enamel composition, wherein the at least one silicone polymer is present in the nail enamel composition in the amount of 0.5 to 10% by weight, wherein the voids expose therethrough a portion of the natural or synthetic nails or polymer film forming base coat.

11. The composition of claim 10, wherein the film forming component is selected from the group consisting of acrylic polymers, styrenated acrylic polymers, acrylic-urethane polymers, vinyl acrylates, polyurethane, polyurethane copolymers, vinyl acetate polymers and vinyl acetate copolymers, olefin polymers and olefin copolymers, and mixture thereof.

12. The composition of claim 10, wherein the at least one silicone polymer is present in the nail enamel composition in the amount of 2 to 4% by weight.

13. The composition of claim 10, wherein the at least one color component comprises a plurality of pigments.

14. The composition of claim 13, further including a plurality of film forming components.

15. The composition of claim 14, further including a plurality of silicone polymers.

16. The composition of claim 10, wherein the at least one silicone polymer is selected from the group consisting of Octamethylcylotetrasiloxane, Polydimethylsiloxane, Methylated Silica, Decamethylcyclopentasiloxane, Dimethylsiloxane, Dimethyl Siloxane, hydroxy-terminated, Hexamethyldisiloxane, Polydimethylsiloxane, Hydroxyl Dimethyl terminated, and mixtures thereof.

17. The composition of claim 10, wherein water is present in the nail enamel composition in the amount of 30% to 50% by weight.

18. The composition of claim 10, wherein the nail enamel composition is devoid of toxic components.

19. An aqueous based decorative nail enamel composition for forming an irregular film containing voids over natural or synthetic nails or a polymer film forming base coat applied thereto upon drying, said voids comprising an opening within the film having a regular, irregular or random shape, the composition comprising:
- water in an amount ranging from 30% to 50% by weight of the composition;
- at least one film forming component in an amount ranging from 15% to 30% by weight of the composition;
- at least one silicone polymer in an amount ranging from 0.5% to 10% by weight of the composition; and
- at least one color component;
- wherein the at least one silicone polymer is present in a sufficient amount wherein a plurality of voids form in a uniform, random or irregular pattern in the at least one film forming component upon drying of the nail enamel composition, wherein the voids expose therethrough a portion of the natural or synthetic nails or polymer film forming base coat.

20. The composition of claim 19, wherein the at least one silicone polymer is selected from the group consisting of Octamethylcylotetrasiloxane, Polydimethylsiloxane, Methylated Silica, Decamethylcyclopentasiloxane, Dimethylsiloxane, Dimethyl Siloxane, hydroxy-terminated, Hexamethyldisiloxane, Hydroxyl Dimethyl terminated, and mixtures thereof.

21. The composition of claim 20, wherein the film forming component is selected from the group consisting of acrylic polymers, styrenated acrylic polymers, acrylic-urethane polymers, vinyl acrylates, polyurethane, polyurethane copolymers, vinyl acetate polymers and vinyl acetate copolymers, olefin polymers and olefin copolymers, and mixtures thereof.

22. The composition of claim 19, wherein the water and the at least one silicone polymer form a homogeneous mixture.

23. The composition of claim 19, wherein the at least one silicone polymer is present in the nail enamel composition in the amount of 2 to 4% by weight.

24. The composition of claim 19, wherein the nail enamel composition is devoid of toxic components.

* * * * *